(12) United States Patent
Chen et al.

(10) Patent No.: US 6,350,883 B1
(45) Date of Patent: Feb. 26, 2002

(54) METHOD FOR PREPARING LACTAM

(75) Inventors: Shien-Chang Chen, Taipei; Fu-Shen Lin, Kaohsiung; Liang-An Hsu, Kaohsiung; Cheng-Lin Tsai, Kaohsiung; Joe-Min Lin, Kaohsiung, all of (TW)

(73) Assignee: Dairen Chemical Corporation (TW)

( * ) Notice: Subject to any disclaimer, the term of this patent is extended or adjusted under 35 U.S.C. 154(b) by 0 days.

(21) Appl. No.: 09/721,285

(22) Filed: Nov. 22, 2000

(30) Foreign Application Priority Data

Apr. 14, 2000 (TW) .......................................... 89106957

(51) Int. Cl.$^7$ .................... C07D 207/267; C07D 201/00
(52) U.S. Cl. ........................................ 548/554; 549/272
(58) Field of Search ........................... 549/272; 548/554

(56) References Cited

U.S. PATENT DOCUMENTS 3,775,431 A    11/1973    Rodewald et al.

FOREIGN PATENT DOCUMENTS

| JP | 47-21420 | 6/1972 |
| JP | 49-20258 | 5/1974 |
| JP | 51-42107 | 11/1976 |
| JP | 6-78304 | 10/1994 |
| JP | 7-10835 | 2/1995 |

*Primary Examiner*—Floyd D. Higel
*Assistant Examiner*—Andrea D'Souza Small
(74) *Attorney, Agent, or Firm*—Peter F. Corless; Christine C. O'Day; Edwards & Angell, LLP

(57) ABSTRACT

The present invention is related to a method for preparing lactam represented by the following formula:

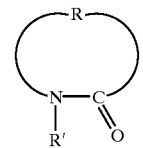

wherein R is $C_{2-10}$ alkylene which may be optionally substituted with $C_{1-6}$ alkyl or phenyl; R' is a hydrogen atom, $C_{1-6}$ alkyl, $C_{1-6}$ hydroxyalkyl or phenyl. The method for preparing lactam comprises an amination reaction using crystalline aluminosilicate zeolites as catalysts under the condition of gas phase in the presence of (a) lactone, (b) amine and/or ammonia and (c) water.

14 Claims, No Drawings

METHOD FOR PREPARING LACTAM

FIELD OF THE INVENTION

The present invention relates to a method for preparing lactam, which comprises an amination reaction using crystalline aluminosilicate zeolites as catalysts under the condition of gas phase in the presence of (a) lactone, (b) amine and/or ammonia and (c) water. The method of the present invention, which uses crystalline aluminosilicate zeolite catalysts, has many advantages including low reaction pressure, high yield per unit time, and short reaction time, etc.

BACKGROUND OF THE INVENTION

Lactam, such as 2-pyrrolidone, N-alkylpyrrolidone, caprolactam etc., is used as a solvent or a polymeric monomer of high molecular compounds. Thus, developing an economic method for preparing lactam is a common industrial requirement.

For example, pyrrolidone may be synthesized by a hydrogenation and an amination reaction with succinic acid, succinic anhydride, maleic acid or maleic anhydride, etc.; caprolactam may be synthesized by a hydrogenation and an amination reaction with cyclohexanone. Moreover, lactam may also be synthesized by an amination of lactone and amine with a method of catalytic reaction or a method of non-catalytic reaction.

Regarding the method of non-catalytic liquid phase reaction, Japanese Patent Application Nos. Sho-47-21420 and Sho-49-20585 disclose a method of reacting an excessive amount of aqueous methylamine solution with γ-butyrolactone and generating N-methylpyrrolidone at a temperature of 200 to 300° C. under 20 to 40 atm. In this method, methylamine is first dissolved in the water, and then reacted with γ-butyrolactone, which is effective for the selectivity of N-methylpyrrolidone. Japanese Patent Application No. Sho-51-42107 discloses a method of dissolving an excessive amount of methylamine in the water, and recycling methylamine in the reaction by water carrying methylamine. Japanese Patent Examined Publication Nos. Hei-6-78304 and Hei-7-10835 disclose an improved method of using secondary or tertiary amine for preparing N-substituted-2-pyrrolidone. However, such non-catalytic liquid phase reactions described above still have many disadvantages, including high-pressure operation and low yield per unit time (i.e., long reaction time), so that it does not yield a beneficial economic effect in the industrial process. Furthermore, in these reactions, industry needs to use large reactor equipment because of the high reaction pressure and the long retention time of the product in the reactor, so that its manufacturing cost is prohibitive.

Regarding the method of catalytic liquid phase reaction, Paul G. Rodewald et al. first proposed in U.S. Pat. No. 3,775,431 in 1973 a process by which lactone is reacted with primary amine and generates lactam using Zeolite X as catalysts. However, for example, in generating N-methylpyrrolidone, the yield of resultant products is still poor although the reaction temperature reaches 300° C., the reaction pressure reaches 500 psig and an excessive amount of methylamine is used, such as where the molar ratio is over 30.

We, the inventors, have broadly and deeply studied the defects of the traditional technique, and found that an amination reaction of lactone and amine and/or ammonia using crystalline aluminosilicate zeolites as catalysts under the condition of gas phase may substantially decrease the reaction pressure of operation and increase the yield of products. We have hereby accomplished the present invention.

DETAILED DESCRIPTION OF THE INVENTION

The present invention is related to a method for preparing lactam represented by the following formula (I):

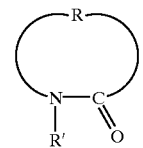

(I)

wherein R is $C_{2-10}$ alkylene which may be optionally substituted with $C_{1-6}$ alkyl or phenyl; R' is a hydrogen atom, $C_{1-6}$ alkyl, $C_{1-6}$ hydroxyalkyl or phenyl. The method for preparing lactam comprises an amination reaction using crystalline aluminosilicate zeolites as catalysts under the condition of gas phase in the presence of (a) lactone, (b) amine and/or ammonia and (c) water.

Lactone, the starting material used in the present invention, may be represented by the following formula (II):

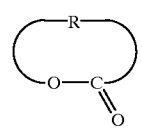

(II)

wherein the definition of R has the same meaning described above.

In the present invention, the example of $C_{2-10}$ alkylene represented by R includes ethylene, propylene, butylene, pentylene, hexylene, heptylene, octylene, nonylene, decylene, etc. $C_{2-10}$ alkylene represented by R may be optionally substituted with $C_{1-6}$ alkyl or phenyl. The example of $C_{1-6}$ alkyl as a substituent includes methyl, ethyl, propyl, butyl, pentyl, hexyl, etc.

The preferred example of lactone used in the present invention includes β-propiolactone, γ-butyrolactone, γ-phenyl-γ-butyrolactone, γ-methyl-γ-butyrolactone, γ-phenyl-γ-methyl-γ-butyrolactone, δ-butyrolactone, γ-valerolactone, γ-caprolactone, ε-caprolactone, δ-hydroxyoctylic acid lactone, δ-hydroxynonylic acid lactone, δ-hydroxydecylic acid lactone, etc., more preferably γ-butyrolactone, γ-caprolactone and ε-caprolactone.

Amine, the starting material used in the present invention, may be primary, secondary or tertiary acyclic amine substituted with one to three $C_{1-6}$ alkyl, $C_{1-6}$ hydroxyalkyl or phenyl. While mono-, di- or tri-$C_{1-6}$- alkylamine, mono-, di- or tri-$C_{1-6}$ alkanolamine is preferred, the example includes mono-, di- or tri-methylamine, mono-, di- or tri-ethylamine, n-propylamine, n-butylamine, n-hexylamine, mono-, di- or tri-ethanolamine, etc.

The present invention utilizes crystalline aluminosilicate zeolites as catalysts for the amination reaction. The crystalline aluminosilicate zeolite has an excellent reactive effect in comparison with other conventional zeolite catalysts, such as mordenite ($Na_8Al_8Si_{40}O_{96}.24H_2O$), Y-type zeolite, etc. In the crystalline aluminosilicate zeolite, silicon dioxide and aluminum oxide are in the ratio of (30 to 500):1, and the constraint index is 1 to 12. The preferred example of the crystalline aluminosilicate zeolite includes ZSM-5, ZSM-11, ZSM-12, ZSM-22, ZSM-34, ZSM-35, ZSM48, etc. ZSM-5 catalysts with three dimensional structures in which the pore size is from 5 to 6 angstrom between small pore molecular sieves (such as A-type zeolite, calcium magnesium zeolite, etc.) and large pore molecular sieves (such as octahedral zeolite, mordenite, etc.) is the most preferred. Therefore, the amination of the present invention is a heterogeneous reaction.

Lactone and amine and/or ammonia used in the amination reaction of the present invention must mix with water in a proper ratio in advance to use as the reactant. In the reactant, the amount of amine and/or ammonia may be more or less than the amount of lactone; in general, an excessive amount of amine and/or ammonia is preferably used.

The molar ratio of lactone and amine and/or ammonia used in the present invention usually ranges from (1:0.5) to (1:30), preferably from (1:1) to (1:10). The increase of the molar ratio of feeding lactone and amine and/or ammonia, such as the increase of 1:5 or more, may shorten the reaction time, as well as easily purify and separate the excessive amount of amine and/or ammonia from the product after the reaction. However, if the molar ratio is over the upper limit, the selectivity may become poor. If the molar ratio is below the lower limit, amine and/or ammonia become the limiting reagent, so that it is difficult to purify and separate the excessive amount of lactone from the product after the reaction.

The molar ratio of lactone and water used in the present invention usually ranges from (1:0.5) to (1:20), preferably from (1:2) to (1:6). If the molar ratio is below the lower limit, the conversion and selectivity of the reaction may obviously become poor. If the molar ratio is over the upper limit, the purification and separation of the product after the reaction may cost excessive amounts of time and energy, although the reaction is not directly affected.

The temperature of the amination reaction used in the present invention ranges from 180 to 400° C., preferably 220 to 320° C. In general, the selectivity of the reaction may be raised with the increase of the temperature. However, if the temperature is over 400° C., undesired by-products may be yielded in addition to the resultant lactam. If the temperature is below 180° C., the reaction may not be carried out rapidly enough to be effective.

Because the acidity of the crystalline aluminosilicate zeolite described above is stronger than aluminum oxide and the reactivity is also strong, the amination reaction of the present invention may be carried out at a pressure which does not destroy the configuration of the catalyst. The pressure used in the reaction usually ranges from 0 to 10 atm., preferably from 1 to 5 atm. While the increase of the pressure may slightly raise the conversion of lactone, the effect is not significant in comparison with other factors affecting the experiment.

The amination reaction of the present invention may be carried out in the fixed bed reactor, the fluid bed reactor, and the other heterogeneous gas phase reactor. If the fixed bed reactor is used, the crystalline aluminosilicate zeolite catalyst described above needs to form shapes for easy packing, such as in grains, tablets, etc.

The gas hourly space velocity (hereinafter sometimes abbreviated as GHSV) used in the amination reaction of the present invention may depend on the reaction of various lactone and amine and/or ammonia. In general, GHSV is 20 to 100000 hr$^{-1}$, preferably 2000 to 50000 hr$^{-1}$. If GHSV is over 100000 hr$^{-1}$, the reaction is not completed, and the conversion is poor. If GHSV is below 20 hr$^{-1}$, undesired by-products may easily result due to the lengthy time of contacting with the catalyst.

The present invention will be further described in the following Examples. However, such Examples are merely used to specify the present invention, and they are not used to restrict the scope of the present invention.

EXAMPLE

Lactone and amine and/or ammonia used in the following Example and Reference Example were well-known compounds or prepared by the conventional methods.

In a given time after the reaction, the product was collected by condensation. The component of the efflux from the outlet was analyzed by HP-6890 gas chromatograph. The conversion of lactone and the selectivity of lactam were calculated according to the following equation (1) and (2):

$$\text{The Conversion of Lactone } (\%) = \frac{\text{The Mole of Feed-in Lactone} - \text{The Mole of Feed-out Lactone}}{\text{The Mole of Feed-in Lactone}} \times 100\% \quad (1)$$

$$\text{The Selectivity of Lactam } (\%) = \frac{\text{The Mole of Lactam Product}}{\text{The Mole of Feed-in Lactone} - \text{The Mole of Feed-out Lactone}} \times 100\% \quad (2)$$

Example 1

ZSM-5 catalyst (40 ml) was packed in the reactor having an inside diameter of 26 mm. The reactants of γ-butyrolactone, methylamine and water were mixed and fed in the ratio of 10:4:6 by weight. The gas hourly space velocity of feeding the mixed reactants was maintained 5050 hr$^{-1}$, and the amination reaction was carried out at 280° C. The product was then collected and analyzed. The conversion of γ-butyrolactone was 99.4%, and the selectivity of N-methyl-2-pyrrolidone was 99.0%.

Reference Example 1

The reactor and catalyst were used the same way as in Example 1, but the reactants were only γ-butyrolactone and methylamine which were mixed and fed in the ratio of 1:18 by weight. The gas hourly space velocity of feeding the mixed reactants was maintained 80000 hr$^{-1}$, and the amination reaction was carried out at 280° C. The product was then collected and analyzed. The conversion of γ-butyrolactone was 35.0%, and the selectivity of N-methyl-2-pyrrolidone was 50.0%.

Example 2

The preparation conditions including the reactor, the catalyst, GHSV and the reaction temperature were all the same as in Example 1 except that the reactants of γ-butyrolactone, methylamine and water were mixed and fed in the ratio of 10:4:6 by weight. The product was then collected and analyzed. The conversion of γ-butyrolactone was 99.7%, and the selectivity of N-methyl-2-pyrrolidone was 99.9%.

Example 3 to 8

The preparation conditions including the reactor, the ratio of feeding the reactants, GHSV and the reaction temperature were all the same as in Example 2 except that various series of ZSM catalysts were used. The product was collected and analyzed. The results are shown in Table 1.

TABLE 1

| Example | Catalyst Type | The Conversion of Butyrolactone | The Selectivity of N-methyl-2-pyrrolidone |
| --- | --- | --- | --- |
| Example 2 | ZSM-5 | 99.7% | 99.9% |
| Example 3 | ZSM-11 | 98.0% | 83.7% |
| Example 4 | ZSM-12 | 97.6% | 81.3% |
| Example 5 | ZSM-22 | 98.2% | 78.0% |
| Example 6 | ZSM-34 | 96.6% | 75.0% |
| Example 7 | ZSM-35 | 97.9% | 69.3% |
| Example 8 | ZSM-48 | 98.1% | 64.4% |

Example 9 to 11

The preparation conditions including the reactor, the catalyst, the ratio of feeding the reactants and the reaction temperature were all the same as in Example 2 except that various GHSV were used. The product was collected and analyzed after stabilization. The results are shown in Table 2.

TABLE 2

| Example | GHSV (hr$^{-1}$) | The Conversion of Butyrolactone | The Selectivity of N-methyl-2-pyrrolidone |
| --- | --- | --- | --- |
| Example 2 | 5050 | 99.7% | 99.9% |
| Example 9 | 7200 | 99.3% | 93.7% |
| Example 10 | 3000 | 100% | 99.9% |
| Example 11 | 1000 | 100% | 97.5% |

Reference Example 2

The preparation conditions including the reactor, the ratio of feeding the reactants, GHSV and the reaction temperature were all the same as in Example 2 except that mordenite (40 ml) was used as the catalyst. The product was then collected and analyzed. The conversion of γ-butyrolactone was 99.5%, and the selectivity of N-methyl-2-pyrrolidone was 58.0%.

Example 12

The reactor and catalyst were used the same way as in Example 1, but the reactants of γ-butyrolactone and water were mixed and fed in the ratio of 1.2:1 by weight, and ammonia gas was continuously feed-in by using a flow controller at the same time. The gas hourly space velocity of feeding the mixed reactants was maintained 3300 hr$^{-1}$, and the amination reaction was carried out at 300° C. The product was then collected and analyzed. The conversion of γ-butyrolactone was 96.0%, and the selectivity of 2-pyrrolidone was 90.0%.

Reference Example 3

The reactor and catalyst were used the same way as in Example 1, but the reactants were only γ-butyrolactone and ammonia gas which were mixed and fed in the ratio of 1:2 by weight. The gas hourly space velocity of feeding the mixed reactants was maintained 2700 hr$^{-1}$, and the amination reaction was carried out at 300° C. The product was then collected and analyzed. The conversion of γ-butyrolactone was 20.0%, and the selectivity of 2-pyrrolidone was 65.0%.

Reference Example 4

The reactor, the ratio of feeding the reactants and the reaction temperature were all the same as in Example 12. Mordenite (40 ml) was used as the catalyst, and the gas hourly space velocity of feeding the mixed reactants was maintained 2700 hr$^{-1}$. The product was then collected and analyzed. The conversion of γ-butyrolactone was 80.0%, and the selectivity of 2-pyrrolidone was 40.0%.

Example 13

The reactor and catalyst were used the same way as in Example 1, but the reactants of γ-butyrolactone, dimethylamine and water were mixed and fed in the ratio of 10:7:11 by weight, and the reactants were continuously feed-in by using a flow controller. The gas hourly space velocity of feeding the mixed reactants was maintained 1000 hr$^{-1}$, and the amination reaction was carried out at 280° C. When the product was collected and analyzed, 10% of methanol was in the product. The conversion of γ-butyrolactone was 98.0%, and the selectivity of N-methyl-2-pyrrolidone was 88.0%.

Example 14

The preparation conditions including the reactor, the catalyst, GHSV and the reaction temperature were all the same as in Example 13 except that the reactants of γ-butyrolactone, trimethylamine and water were mixed and fed in the ratio of 10:9.3:11 by weight. When the product was collected and analyzed, 8% of methanol was in the product. The conversion of γ-butyrolactone was 95.0%, and the selectivity of N-methyl-2-pyrrolidone was 79.0%.

Reference Example 5

The preparation conditions including the reactor, the ratio of feeding the reactants, GHSV and the reaction temperature were all the same as in Example 13 except that Y-type zeolite (40 ml) was used as the catalyst. When the product was collected and analyzed, 6.6% of methanol was in the product. The conversion of γ-butyrolactone was 95.0%, and the selectivity of N-methyl-2-pyrrolidone was 51.0%.

Example 15

The preparation conditions including the reactor, the catalyst, GHSV and the reaction temperature were all the same as in Example 13 except that the reactants of γ-butyrolactone, ethylamine and water were mixed and fed in the ratio of 10:7:13.6 by weight. The product was then collected and analyzed. The conversion of γ-butyrolactone was 98.0%, and the selectivity of methyl-2-pyrrolidone was 79.0%.

Example 16

The preparation conditions including the reactor, the catalyst, GHSV and the reaction temperature were all the same as in Example 13 except that the reactants of γ-butyrolactone, triethylamine and water were mixed and fed in the ratio of 10:16.4:14.6 by weight. When the product was collected and analyzed, 13% of ethanol was in the product. The conversion of γ-butyrolactone was 95.0%, and the selectivity of N-ethyl-2-pyrrolidone was 68.0%.

Example 17

The preparation conditions including the reactor, the catalyst, GHSV and the reaction temperature were all the same as in Example 13 except that the reactants of γ-butyrolactone, ethanolamine and water were mixed and fed in the ratio of 7:5:6 by weight. The product was then collected and analyzed. The conversion of γ-butyrolactone was 92.0%, and the selectivity of N-(β-ethyl)-2-pyrrolidone was 69.0%.

According to the above Examples and Reference Examples, the conversion and selectivity of the reaction were found to be very poor when the ratio of water in the reactants was too low or even non-existent (i.e., Reference Examples 1 and 3); thus it was demonstrated that water was a necessary reactant in the present invention. Since the selectivity of lactam was not raised when the conventional mordenite or Y-type zeolite was used as the catalyst (i.e., Reference Examples 2, 4 and 5), it was demonstrated that the crystalline aluminosilicate zeolite of the present invention raised the yield per unit time.

In addition, compared with the conventional technique, the conditions of generating lactam vary with the kinds of amine utilized when non-catalytic liquid phase amination reaction is used; however, all of the reactions had to be carried out at a high pressure. Using the crystalline aluminosilicate zeolite of the present invention may rapidly obtain the desired lactam at a low pressure.

It is understood that variations and modifications can be effected without departing from the spirit or scope of the invention as set forth in the following claims.

What is claimed is:

1. A method for preparing lactam represented by the following formula (I):

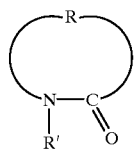

(I)

wherein R is $C_{2-10}$ alkylene which may be optionally substituted with $C_{1-6}$ alkyl or phenyl; R' is a hydrogen atom, $C_{1-6}$ alkyl, $C_{1-6}$ hydroxyalkyl or phenyl; which comprises an amination reaction using crystalline aluminosilicate zeolites as catalysts under the condition of gas phase in the presence of (a) lactone, (b) amine and/or ammonia and (c) water;

wherein said lactone is represented by the following formula (II):

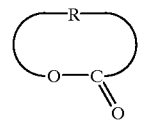

(II)

wherein the definition of R has the same meaning as described above;

wherein said amine is a primary, secondary or tertiary acyclic amine substituted with one to three $C_{1-6}$ alkyl, $C_{1-6}$ hydroxyalkyl or phenyl.

2. A method of claim 1, wherein said lactone is β-propiolactone, γ-butyrolactone, δ-butyrolactone, γ-valerolactone, γ-caprolactone, ε-caprolactone, δ-hydroxyoctylic acid lactone, δ-hydroxynonylic acid lactone, or δ-hydroxydecylic acid lactone.

3. A method of claim 1, wherein said amine is mono-, di- or tri-$C_{1-6}$ alkylamine, mono-, di- or tri-$C_{1-6}$ alkanolamine.

4. A method of claim 3, wherein said amine is mono-, di- or tri-methylamine, mono-, di- or tri-ethylamine, mono-, di- or tri-ethanolamine.

5. A method of claim 1, wherein the molar ratio of silicon dioxide and aluminum oxide in said crystalline aluminosilicate zeolite is (30 to 500):1.

6. A method of claim 1, wherein the constraint index of said crystalline aluminosilicate zeolite is 1 to 12.

7. A method of any one of claim 1 to claim 6, wherein said crystalline aluminosilicate zeolite is selected from a group consisting of ZSM-5, ZSM-11, ZSM-12, ZSM-22, ZSM-34, ZSM-35 and ZSM-48.

8. A method of claim 7, wherein said crystalline aluminosilicate zeolite is ZSM-5.

9. A method of claim 1, wherein the molar ratio of feeding said lactone and said amine and/or ammonia ranges from (1:0.5) to (1:30).

10. A method of claim 1, wherein the molar ratio of feeding said lactone and said water ranges from (1:0.5) to (1:20).

11. A method of claim 1, wherein the temperature of said amination reaction ranges from 180 to 400° C.

12. A method of claim 1, wherein the pressure of said amination reaction ranges from 0 to 10 atm.

13. A method of claim 1, wherein the gas hourly space velocity (GHSV) of said amination reaction is 20 to 100000 $hr^{-1}$.

14. A method of claim 1, wherein the amination reaction is carried out in the fixed bed reactor or fluid bed reactor.

* * * * *